United States Patent
Xiao et al.

(10) Patent No.: US 11,925,403 B2
(45) Date of Patent: Mar. 12, 2024

(54) CRYOABLATION CATHETER, CRYOABLATION OPERATING APPARATUS AND CRYOABLATION EQUIPMENT

(71) Applicant: Piedmont Medsystems (Zhuhai) Co., Ltd., Zhuhai (CN)

(72) Inventors: Jiahua Xiao, Zhuhai (CN); Alan De La Rama, Zhuhai (CN); Cary Kunihiko Hata, Zhuhai (CN)

(73) Assignee: Piedmont Medsystems (Zhuhai) Co., Ltd., Guangdong (CN)

( * ) Notice: Subject to any disclaimer, the term of this patent is extended or adjusted under 35 U.S.C. 154(b) by 359 days.

(21) Appl. No.: 17/046,873

(22) PCT Filed: Apr. 12, 2019

(86) PCT No.: PCT/CN2019/082540
§ 371 (c)(1),
(2) Date: Oct. 12, 2020

(87) PCT Pub. No.: WO2019/196943
PCT Pub. Date: Oct. 17, 2019

(65) Prior Publication Data
US 2021/0045795 A1    Feb. 18, 2021

(30) Foreign Application Priority Data
Apr. 13, 2018   (CN) .......................... 201810330832.8

(51) Int. Cl.
*A61B 18/02*    (2006.01)
*A61B 18/00*    (2006.01)

(52) U.S. Cl.
CPC .... *A61B 18/02* (2013.01); *A61B 2018/00023* (2013.01); *A61B 2018/00041* (2013.01);
(Continued)

(58) Field of Classification Search
CPC .......... A61B 18/02; A61B 2018/00023; A61B 2018/00041; A61B 2018/00101;
(Continued)

(56) References Cited

U.S. PATENT DOCUMENTS 5,458,574 A    10/1995 Machold et al.
6,245,064 B1   6/2001  Lesh et al.
(Continued)

FOREIGN PATENT DOCUMENTS

CN    102098972 A    6/2011
CN    105581838 A    5/2016
(Continued)

OTHER PUBLICATIONS

International Search Report; National Intellectual Property Administration, PRC; International Application No. PCT/CN2019/082540; dated Jul. 11, 2019; 8 pages.
(Continued)

*Primary Examiner* — Joanne M Rodden
*Assistant Examiner* — Matthew David Becton
(74) *Attorney, Agent, or Firm* — Taft Stettinius & Hollister LLP

(57) ABSTRACT

A cryoablation catheter, including a first capsule body, a core tube and a heat insulation part, wherein the first capsule body is mounted at a front end of the core tube, and has a front end area adapted for fitting to myocardial tissue during a cryoablation process and a rear end area exposed to blood; the core tube has a first looping path provided therein which is adapted for a first fluid with low temperature to be filled into or flow out of the first capsule body; the heat insulation part is at least partially fitting to the rear end area, and is adapted for reducing heat exchange efficiency between the first fluid and the blood in an atrium. The cryoablation operating apparatus and the cryoablation equipment thereof
(Continued)

can effectively reduce the heat exchange between the cryoablation catheter and the blood during a cryoablation process.

4 Claims, 3 Drawing Sheets

(52) U.S. Cl.
CPC .......... *A61B 2018/00101* (2013.01); *A61B 2018/0022* (2013.01); *A61B 2018/00255* (2013.01); *A61B 2018/00261* (2013.01); *A61B 2018/00351* (2013.01); *A61B 2018/00375* (2013.01); *A61B 2018/00577* (2013.01); *A61B 2018/0212* (2013.01); *A61B 2018/025* (2013.01); *A61B 2018/0293* (2013.01)

(58) Field of Classification Search
CPC .......... A61B 2018/00255; A61B 2018/00261; A61B 2018/00375; A61B 2018/00577; A61B 2018/0212; A61B 2018/025; A61B 2018/0293

See application file for complete search history.

(56) References Cited

U.S. PATENT DOCUMENTS

| | | | |
|---|---|---|---|
| 6,602,276 B2 * | 8/2003 | Dobak, III | A61F 7/123 607/104 |
| 6,872,205 B2 | 3/2005 | Lesh et al. | |
| 9,060,754 B2 * | 6/2015 | Buckley | A61B 18/02 |
| 2002/0045893 A1 * | 4/2002 | Lane | A61B 18/02 606/21 |
| 2010/0100087 A1 | 4/2010 | Mazzone et al. | |
| 2010/0234838 A1 | 9/2010 | Watson | |
| 2011/0184400 A1 | 7/2011 | Pageard | |
| 2011/0190751 A1 * | 8/2011 | Ingle | A61B 18/02 606/21 |
| 2012/0089047 A1 * | 4/2012 | Ryba | A61B 18/02 600/300 |
| 2013/0197499 A1 * | 8/2013 | Lalonde | A61B 18/02 606/21 |
| 2021/0077173 A1 | 3/2021 | Diao et al. | |

FOREIGN PATENT DOCUMENTS

| | | |
|---|---|---|
| CN | 106691676 A | 5/2017 |
| CN | 107411815 A | 12/2017 |
| CN | 107440782 A | 12/2017 |
| CN | 108309432 A | 7/2018 |
| CN | 208926581 U | 6/2019 |
| EP | 3120792 A1 | 1/2017 |
| WO | 2017047543 A1 | 3/2017 |
| WO | WO-2017047543 A1 * | 3/2017 .......... A61B 18/02 |

OTHER PUBLICATIONS

Written Opinion of the International Searching Authority; National Intellectual Property Administration, PRC; International Application No. PCT/CN2019/082540; dated Jul. 11, 2019; 6 pages.

Extended European Search Report; European Patent Office; Application No. 19785353.4; dated May 10, 2021; 7 pages.

Japanese Office Action; Japanese Patent Office; Japanese Application No. 2021-504568; dated Nov. 8, 2021; 9 pages.

International Search Report; National Intellectual Property Administration, PRC; International Application No. PCT/CN2019/082540; dated Jul. 11, 2019; 9 pages.

Written Opinion of the International Searching Authority; National Intellectual Property Administration, PRC; International Application No. PCT/CN2019/082540; dated Jul. 11, 2019; 5 pages.

* cited by examiner

US 11,925,403 B2

CRYOABLATION CATHETER, CRYOABLATION OPERATING APPARATUS AND CRYOABLATION EQUIPMENT

CROSS REFERENCE TO RELATED APPLICATIONS

This application is a U.S. national stage filing of International Patent Application No. PCT/CN2019/082540 filed Apr. 12, 2019, which claims priority to Chinese Patent Application No. 201810330832.8 filed Apr. 13, 2018, the contents of each application are hereby incorporated by reference in their entirety.

TECHNICAL FIELD

The present application relates to the field of ablation technology, and particularly relates to a cryoablation catheter, a cryoablation operating apparatus and a cryoablation equipment.

BACKGROUND

Atrial fibrillation is a medical disease of abnormal electrical activity in the heart. At present, the medical profession tends to think the electrical signal that causes atrial fibrillation originates from the muscle sleeves on the outer sides of the four pulmonary veins (two left veins and two right veins). Therefore, one way to treat atrial fibrillation is to disconnect the electrical signal communication between the atrial tissue and the muscle sleeves on the outer sides of the pulmonary veins, which is generally realized by ablating a part of the myocardial tissue. Catheter ablation is currently a most commonly-used method for ablating myocardial tissue. Cryoablation is one kind of catheter ablation emerging in recent years, and has advantages such as less pain for a patient in an operation process and less sequela, as well as advantages such as low difficulty of operation and short training process.

As shown in FIG. 1, in a cryoablation process, an ablation catheter with a capsule body is delivered to an atrium via a peripheral venous vessel, and after the catheter arrives at the atrium, a low-temperature fluid is filled into the capsule body, the capsule body expands and abuts against an opening of a pulmonary vein, relative slipping between the capsule body and the myocardial tissue is prevented by a cryosorption effect, and the low temperature is utilized to cause necrosis of the myocardial tissue, so that any hyperexcitability of the pulmonary vein which would cause an atrial fibrillation attack is blocked within the pulmonary vein. As compared to conventional radiofrequency ablation, cryoablation has advantages of stable target spot and good contact tightness, and more importantly, because a low temperature is used for the ablation, the necrotic myocardial tissue would be absorbed by the body, and therefore the probability of postoperative embolization is effectively reduced.

However, cryoablation catheters in prior arts usually used a spherical soft capsule at a front end thereof to store the low-temperature fluid, which has certain defects in practical use. As the low-temperature fluid needs to be stored in the spherical soft capsule during a freezing process, and except the part in contact with the myocardial cells, the other part of the spherical soft capsule is always immersed in the blood of the atrium during the whole freezing process, thus, in the freezing process, there is a large area of contact between the blood and the soft capsule, which leads to a large area of contact heat exchange and greatly reduces the temperature of the blood, such low-temperature blood would be pumped to other organs of the body by the beating of the heart, and normal functioning of these organs would be adversely affected, which brings harmful influence on the health of the patient.

SUMMARY OF THE INVENTION

Therefore, a technical problem to be solved by the present application is how to overcome the defects in prior arts that too much heat exchange happens between the blood in an atrium and a cryoablation catheter when performing cryoablation on myocardial tissue and accordingly to provide a cryoablation catheter that can reduce heat exchange with the blood.

Another technical problem to be solved by the present application is how to overcome the defects in prior arts that too much heat exchange happens between the blood in an atrium and a cryoablation operating apparatus when performing cryoablation on myocardial tissue and accordingly to provide a cryoablation operating apparatus that can reduce heat exchange with the blood.

Another technical problem to be solved by the present application is how to overcome the defects in prior arts that too much heat exchange happens between the blood in an atrium and a cryoablation equipment when performing cryoablation on myocardial tissue and accordingly to provide a cryoablation equipment that can reduce heat exchange with the blood.

Thus, the technical solutions provided by the present application are as follows:

A cryoablation catheter, comprising:
  a first capsule body, mounted at a front end of a core tube, and having a front end area adapted for fitting to myocardial tissue during a cryoablation process and a rear end area exposed to blood;
  the core tube, having a first looping path provided therein which is adapted for a first fluid with low temperature to be filled into or flow out of the first capsule body; and
  a heat insulation part, at least partially fitting to the rear end area, adapted for reducing heat exchange efficiency between the first fluid and the blood in an atrium.

As a preferable technical solution, the heat insulation part at least covers a part of the rear end area, and the heat insulation part is filled with a second fluid therein, the second fluid has a temperature higher than that of the first fluid.

As a preferable technical solution, a partition membrane is provided in the first capsule body, and the partition membrane is adapted for dividing the space in the first capsule body into a cryogen chamber adapted for accommodating the first fluid and the heat insulation part adapted for accommodating the second fluid.

As a preferable technical solution, the heat insulation part is a second capsule body provided inside the first capsule body, at least part of the second capsule body fits to an inner wall of the rear end area.

As a preferable technical solution, the second capsule body has an opening communicated with an interior of the first capsule body, and the first looping path has an outflow port for the first fluid located inside the second capsule body.

As a preferable technical solution, the second capsule body has elasticity for supporting the first capsule body to form a stepped shape.

As a preferable technical solution, the cryoablation catheter further comprises: a sheath, sleeved outside the core tube, and adapted for accommodating both the first capsule body and the second capsule body in a collapsed state;
wherein the core tube is adapted for driving both the first capsule body and the second capsule body to protrude out of or retract into the sheath;
wherein the sheath is adapted for constraining elastic deformation of the second capsule body.

As a preferable technical solution, the second capsule body is not communicated with the first capsule body, and the second capsule body is adapted for accommodating the second fluid with a temperature higher than that of the first fluid during the cryoablation process.

As a preferable technical solution, the heat insulation part is a third capsule body provided outside the rear end area, an outer wall of the third capsule body at least partially fits to the rear end area, and the third capsule body is adapted for accommodating the second fluid during the cryoablation process.

As a preferable technical solution, the third capsule body has a maximum outer diameter larger than that of the first capsule body.

As a preferable technical solution, a second looping path for the second fluid to be filled into or flow out of the heat insulation part is provided in the core tube.

As a preferable technical solution, at least one telescopic structure is provided at the front end of the core tube, the telescopic structure is adapted for increasing a distance between two binding ends of the first capsule body on the core tube when the telescopic structure protrudes out.

A cryoablation operating apparatus, comprising:
a handle, connected to the cryoablation catheter according to the aforementioned technical solutions; and
an actuator, connected to the core tube according to the aforementioned technical solutions.

A cryoablation equipment, comprising the cryoablation catheter according to the aforementioned technical solutions or comprising the aforementioned cryoablation operating apparatus.

The technical solutions of the present application have the following advantages:

1. In the technical solutions provided by the present application, the cryoablation catheter comprises a first capsule body, a core tube and a heat insulation part, wherein the first capsule body is mounted at a front end of the core tube, and has a front end area adapted for fitting to myocardial tissue during a cryoablation process and a rear end area exposed to blood; the core tube has a first looping path provided therein which is adapted for a first fluid with low temperature to be filled into or flow out of the first capsule body; the heat insulation part is at least partially fitting to the rear end area, and is adapted for reducing heat exchange efficiency between the first fluid and the blood in an atrium. Before an operation is started, the first capsule body is vacuumized and collapses to fit to a front end of the core tube. After the operation is started, the core tube drives the first capsule body to protrude along a blood vessel and into an atrium, then the first looping path is used to fill the first capsule body with a first fluid for cryoablation, and when the first capsule body is expanded, the front end area thereof is used to contact the myocardial tissue to perform cryoablation on the myocardial tissue. At this time, as the rear end area of the first capsule body has the heat insulation part, the heat exchange efficiency between the blood and the low-temperature fluid in the first capsule body is reduced under the action of the heat insulation part, so that the heat exchange speed is reduced to ensure that the first fluid does not take too much heat from the blood via the rear end area, thereby effectively alleviating the stress caused to the patient's body by lowering of the blood temperature, and preventing any harmful influence on the health of the patient. From another perspective, the success rate of cryoablation operation can be guaranteed, and the postoperative recovery time is shortened.

2. In the technical solutions provided by the present application, a partition membrane is provided in the first capsule body, and the partition membrane is adapted for dividing the space in the first capsule body into a cryogen chamber adapted for accommodating the first fluid and the heat insulation part adapted for accommodating the second fluid. This heat insulation part is located inside the first capsule body, and the partition membrane can be integrally formed with the first capsule body, so as to lower the difficulty of manufacturing, and it is beneficial for controlling the cost of the cryoablation catheter, meanwhile, as the heat insulation part is filled with the second fluid, heat exchange between the first fluid and the blood in the atrium is effectively blocked, thereby effectively prevent the temperature of the blood from lowering.

3. In the technical solutions provided by the present application, the heat insulation part is a second capsule body provided inside the first capsule body, at least part of the second capsule body fits to an inner wall of the rear end area. By providing a second capsule body inside the first capsule body, in one aspect, as the second capsule body fits to the rear end area, the wall thickness at the fitting location is increased, so as to block the heat exchange between the blood and the first fluid in the capsule body and slow down the decreasing of temperature of the blood; in another aspect, the existence of the second capsule body provides a space for filling in another fluid with a temperature higher than that of the first fluid, so as to block the heat exchange between the blood and the first fluid more thoroughly.

4. In the technical solutions provided by the present application, the second capsule body has an opening communicated with an interior of the first capsule body, and the first looping path has an outflow port for the first fluid located inside the second capsule body. By designing the second capsule body in the aforementioned form, as the temperature of the first fluid rises after the first fluid flows into the interior of the first capsule body and comes into contact with the myocardial tissue, the first fluid with an increased temperature then flows into the second capsule body through the opening of the second capsule body, which makes the temperature in the second capsule body higher than the temperature in the first capsule body, so as to hinder the heat exchange between the low-temperature first fluid and the blood, thereby preventing the temperature of the blood from lowering.

5. In the technical solutions provided by the present application, the second capsule body has elasticity for supporting the first capsule body to form a stepped shape. In this technical solution, as the second capsule body is communicated with the interior of the first capsule body, in order to prevent the second capsule body from collapsing inside the first capsule body due to impinging of the first fluid, the second capsule body is designed to be made of an elastic material, which in one aspect can prevent the second capsule body from collapsing and in another aspect can also support the first capsule body to make the positioning of the first capsule body onto the opening of the vein more secured, thereby lowering the difficulty of operation and increasing the success rate of operation.

6. In the technical solutions provided by the present application, the cryoablation catheter further comprises a sheath sleeved outside the core tube and adapted for accommodating both the first capsule body and the second capsule body in a collapsed state; wherein the core tube is adapted for driving both the first capsule body and the second capsule body to protrude out of or retract into the sheath; and wherein the sheath is adapted for constraining elastic deformation of the second capsule body. The first capsule body may fit to the front end of the core tube after being vacuumized, but the second capsule body exerts an expanding elastic force, at this time, the sheath can constrain the elastic deformation of the second capsule body, so as to avoid the fact that the second capsule body in a free state is unable to protrude into a blood vessel, thereby ensuring a smooth operation.

7. In the technical solutions provided by the present application, the second capsule body is not communicated with the first capsule body, and the second capsule body is adapted for accommodating the second fluid with a temperature higher than that of the first fluid during the cryoablation process. By designing the second capsule body in an closed form, the second capsule body accommodates the second fluid therein and is completely independent from the substance in the first capsule body, so that the temperatures of the first fluid and the second fluid can be controlled individually, therefore, such design can provide a structural basis to allow the temperature of the second fluid to stay as close to the human body temperature as possible, so as to provide the possibility of reducing the influence of the low-temperature fluid on the blood during the cryoablation process to a minimum.

8. In the technical solutions provided by the present application, the heat insulation part is a third capsule body provided outside the rear end area, an outer wall of the third capsule body at least partially fits to the rear end area, and the third capsule body is adapted for accommodating the second fluid during the cryoablation process. When the third capsule body is located outside the rear end area, because the two capsule bodies are relatively independently arranged, in one aspect, the heat conduction between the rear end area and the blood can be blocked by the fitting of the third capsule body onto the first capsule body, in another aspect, the two spaced capsule bodies are easier to manufacture, so that the use cost of the consumptive material of capsule bodies can be reduced.

9. In the technical solutions provided by the present application, the third capsule body has a maximum outer diameter larger than that of the first capsule body. When the maximum outer diameter of the third capsule body is larger than the maximum outer diameter of the first capsule body, in one aspect, during the cryoablation process, the third capsule body can abut against the opening of the pulmonary vein, with the first capsule body slightly protruding into the pulmonary vein, such a form can have a better blocking effect, wherein the third capsule body on the side of the atrium can completely block the blood from contacting the first capsule body; in another aspect, the third capsule body also has certain positioning effect to allow the entire capsule body assembly to more smoothly fit to the opening of the pulmonary vein, thereby lowering the difficulty of cryoablation operation, and preventing the capsule body assembly from slipping off the target tissue during the cryoablation process.

10. In the technical solutions provided by the present application, a second looping path for the second fluid to be filled into or flow out of the heat insulation part is provided in the core tube. The second looping path can be utilized to circulate the second fluid during the cryoablation process, and when the circulated second fluid has a constant temperature, it can be ensured that the temperature inside the second capsule body is always in a constant state, without too much fluctuation of temperature, so that the stability and controllability of the operation process can be increased.

11. In the technical solutions provided by the present application, at least one telescopic structure is provided at the front end of the core tube, the telescopic structure is adapted for increasing a distance between two binding ends of the first capsule body on the core tube when the telescopic structure protrudes out. In an initial stage at the start of the operation, the first capsule body is vacuumized, and the capsule body in a thin-film state adheres to the front end of the core tube, at this time, the existence of the telescopic structure can allow the distance between the two binding ends of the first capsule body on the core tube to be increased, therefore, under the action of the telescopic end thereof, the collapsed first capsule body is prevented from piling up at the front end of the core tube and enlarging the volume of the front end of the core tube, so that the cryoablation catheter can be smoothly introduced from the blood vessel into the atrium, and clogging of the blood vessel can be prevented.

In summary, the technical solutions provided by the present application can effectively reduce the heat exchange efficiency between the cryoablation catheter and the blood during a cryoablation process, prevent any harmful influence on the health of the patient caused by a lowered blood temperature, increase the stability and controllability of the operation process, and shorten the postoperative recovery time for the patient.

BRIEF DESCRIPTION OF THE DRAWINGS

In order to describe the technical solutions more clearly in the specific embodiments of the present application or in the prior art, hereinafter, the appended drawings used for describing the specific embodiments or the prior art will be briefly introduced. Apparently, the drawings described below show only some embodiments of present application, and for a person skilled in the art, without expenditure of creative labor, other drawings can be derived on the basis of these appended drawings.

REFERENCE SIGNS

Figure 1:
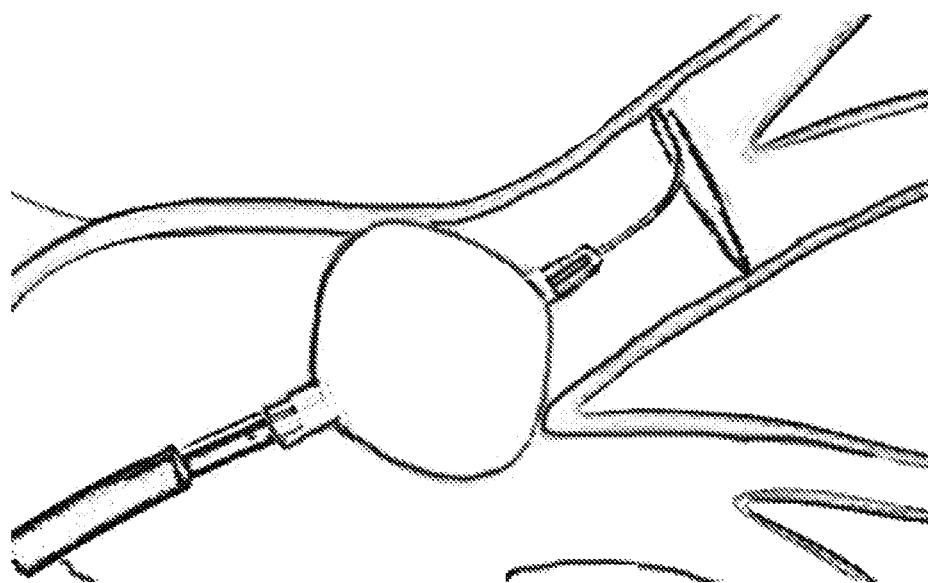
FIG. 1 is a structural schematic view of a cryoablation catheter of the prior art working in an atrium.

1—sheath, 2—partition membrane, 3—core tube, 31—first looping path, 32—second looping path, 4—first capsule body, 41—front end area, 42—rear end area, 43—cryogen chamber, 5—heat insulation part, 51—second capsule body, 52—third capsule body, 6—telescopic structure.

DETAILED DESCRIPTION OF EMBODIMENTS

A clear and complete description of the technical solutions of the present application is given below, in conjunction with the appended drawings. Apparently, the described embodiments are a part, but not all, of the embodiments of the present application. All the other embodiments, derived by a person skilled in the art on the basis of the embodiments described in the present application without expenditure of creative labor, are included in the protection scope of the present application.

In the description of the present application, it needs to be noted that, terms such as "center", "above", "below", "left", "right", "vertical", "horizontal", "inside", "outside" refer to the orientation or positional relation based on the illustration of the drawings, which is merely for facilitating and simplifying the description of the present invention, not for indicating or implying that the referred apparatus or component must have a particular orientation or must be configured or operated in a particular orientation, therefore is not to be construed as a limitation towards the present application. In addition, terms such as "first", "second", "third" are merely for the purpose of description, and are not to be construed as an indication or implication of relative importance thereof.

In the description of the present application, it needs to be noted that, unless specifically defined or restricted otherwise, terms such as "mount", "interconnect", "connect" should be broadly construed, for example, they may be fixed connection or detachable connection or integral connection; they may be mechanical connection or electrical connection; they may be direct connection, or indirect connection via an intermediate medium, or internal communication between two units. For a person skilled in the art, the specific meaning of the aforementioned terms in the present application can be understood according to specific situations thereof.

Furthermore, the technical features involved in the various embodiments of the present application described below can be combined with one another as long as they do not conflict with one another.

Embodiment 1

FIG. 2 to FIG. 5 show Embodiment 1 of the present application. This embodiment provides a cryoablation catheter for ablating a part of the myocardial tissue in an atrium, which is usually used for treating atrial fibrillation.

The cryoablation catheter provided in this embodiment comprises a first capsule body 4, a core tube 3 and a heat insulation part 5, wherein the first capsule body 4 is mounted at a front end of the core tube 3, and has a front end area 41 adapted for fitting to myocardial tissue during a cryoablation process and a rear end area 42 exposed to blood; the core tube 3 has a first looping path 31 provided therein which is adapted for a first fluid with low temperature to be filled into or flow out of the first capsule body 4; the heat insulation part 5 is at least partially fitting to the rear end area 42, and is adapted for reducing heat exchange efficiency between the first fluid and the blood in an atrium.

Before an operation is started, the first capsule body 4 is vacuumized and collapses to fit to a front end of the core tube 3. After the operation is started, the core tube 3 drives the first capsule body 4 to protrude along a blood vessel and into an atrium, then the first looping path 31 is used to fill the first capsule body 4 with a first fluid for cryoablation, and when the first capsule body 4 is expanded, the front end area 41 thereof is used to contact the myocardial tissue to perform cryoablation on the myocardial tissue. At this time, as the rear end area 42 of the first capsule body 4 has the heat insulation part 5, the heat exchange efficiency between the blood and the low-temperature fluid in the first capsule body 4 is reduced under the action of the heat insulation part 5, so that the heat exchange speed is reduced to ensure that the first fluid does not take too much heat from the blood via the rear end area 42, thereby effectively alleviating the stress caused to the patient's body by lowering of the blood temperature, and preventing any harmful influence on the health of the patient. From another perspective, the success rate of cryoablation operation can be guaranteed, and the postoperative recovery time is shortened.

As a further improved implementation of the heat insulation part 5, the heat insulation part 5 at least covers a part of the rear end area 42, and the heat insulation part 5 is filled with a second fluid therein, the second fluid has a temperature higher than that of the first fluid.

Figure 2:
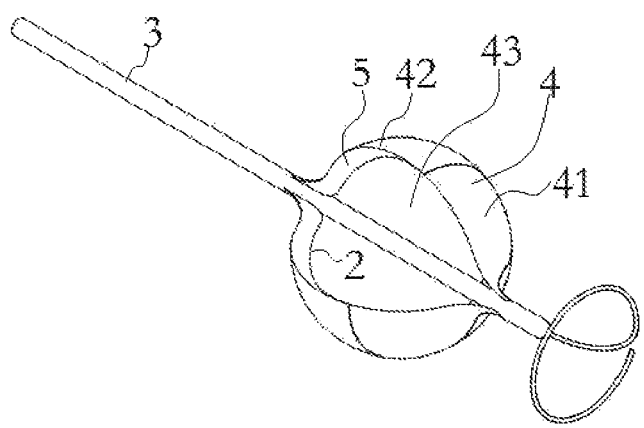
FIG. 2 is a stereogram of a first implementation of a cryoablation catheter provided in Embodiment 1 of the present application.

As shown in FIG. 2, as an alternative implementation of the heat insulation part 5, a partition membrane 2 is provided in the first capsule body 4, and the partition membrane 2 is adapted for dividing the space in the first capsule body 4 into a cryogen chamber 43 adapted for accommodating the first fluid and the heat insulation part 5 adapted for accommodating the second fluid. This form of heat insulation part 5 is located inside the first capsule body 4, and the partition membrane 2 can be integrally formed with the first capsule body 4, so as to lower the difficulty of manufacturing, and it is beneficial for controlling the cost of the cryoablation catheter, meanwhile, as the heat insulation part 5 is filled with the second fluid, heat exchange between the first fluid and the blood in the atrium can be effectively blocked, thereby effectively prevent the temperature of the blood from lowering.

Figure 3:
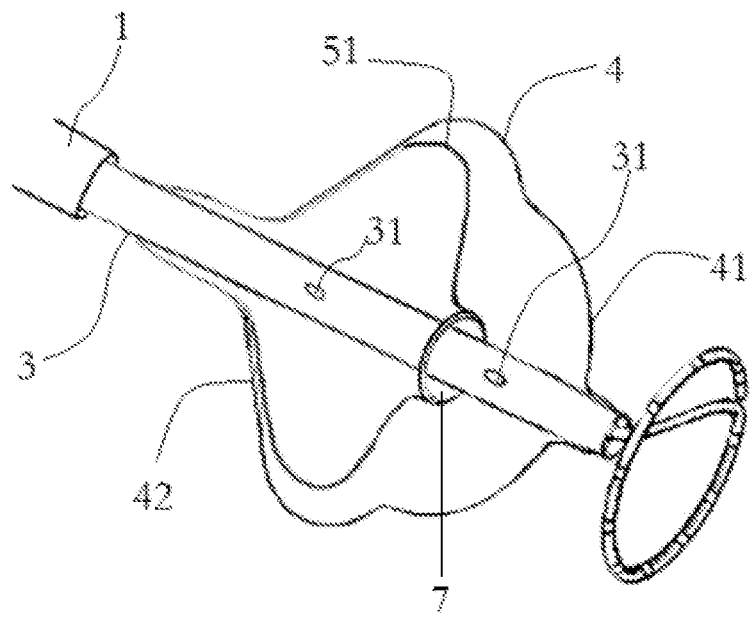
FIG. 3 is a stereogram of a second implementation of a cryoablation catheter provided in Embodiment 1 of the present application.
Figure 4:
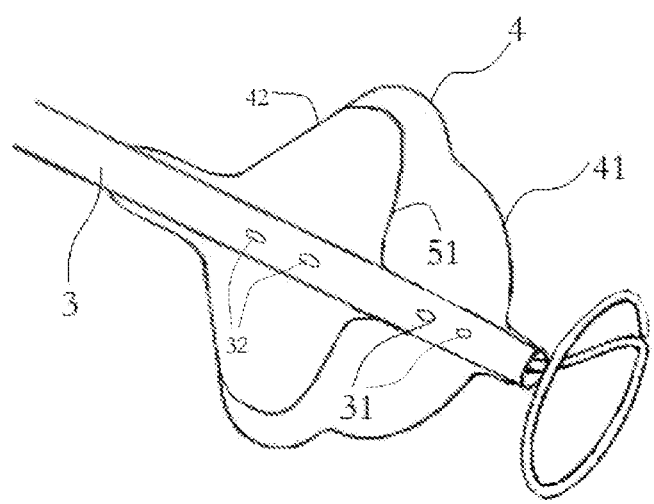
FIG. 4 is a stereogram of a third implementation of a cryoablation catheter provided in Embodiment 1 of the present application.

As shown in FIG. 3 and FIG. 4, as another alternative implementation of the heat insulation part 5, the heat insulation part 5 is a second capsule body 51 provided inside the first capsule body 4, at least part of the second capsule body 51 fits to an inner wall of the rear end area 42. By providing a second capsule body 51 inside the first capsule body 4, in one aspect, as the second capsule body 51 fits to the rear end area 42, the wall thickness at the fitting location is increased, so as to block the heat exchange between the blood and the first fluid in the capsule body and slow down the decreasing of temperature of the blood is reduced; in another aspect, the existence of the second capsule body 51 provides space for filling in another fluid with a temperature higher than that of the first fluid, so as to block the heat exchange between the blood and the first fluid more thoroughly.

As shown in FIG. 3, as an alternative implementation of the second capsule body 51, the second capsule body 51 has an opening 7 communicated with an interior of the first capsule body 4, and the first looping path 31 has an outflow port for the first fluid located inside the second capsule body 51. By designing the second capsule body 51 in the aforementioned form, as the temperature of the first fluid rises after the first fluid flows into the interior of the first capsule body 4 and comes into contact with the myocardial tissue, the first fluid with an increased temperature then flows into the second capsule body 51 through the opening 7 of the second capsule body 51, which makes the temperature in the second capsule body 51 higher than the temperature in the first capsule body 4, so as to hinder the heat exchange between the low-temperature first fluid and the blood, thereby preventing the temperature of the blood from lowering.

As a further improved implementation of the above-mentioned second capsule body 51, the second capsule body 51 has elasticity for supporting the first capsule body 4 to form a stepped shape. In this technical solution, as the second capsule body 51 is communicated with the interior of the first capsule body 4, in order to prevent the second capsule body 51 from collapsing inside the first capsule body 4 due to impinging of the first fluid, the second capsule body 51 is designed to be made of an elastic material, which in one aspect can prevent the second capsule body 51 from collapsing and in another aspect can also support the first capsule body 4 to make the positioning of the first capsule body 4 onto the opening of the vein more secured, thereby lowering the difficulty of operation and increasing the success rate of operation.

In order to ensure that the above-mentioned second capsule body 51 can smoothly enter a blood vessel, the cryoablation catheter further comprises a sheath 1, the sheath 1 is sleeved outside the core tube 3 and adapted for accommodating both the first capsule body 4 and the second capsule body 51 in a collapsed state; the core tube 3 is adapted for driving both the first capsule body 4 and the second capsule body 51 to protrude out of or retract into the sheath 1; and the sheath 1 is adapted for constraining elastic deformation of the second capsule body 51. The first capsule body 4 may fit to the front end of the core tube 3 after being vacuumized, but the second capsule body 51 exerts an expanding elastic force, at this time, the sheath 1 can constrain the elastic deformation of the second capsule body 51, so as to avoid the fact that the second capsule body 51 in a free state from is unable to protrude into a blood vessel, thereby ensuring a smooth operation.

As shown in FIG. 4, as another alternative implementation of the second capsule body 51, the second capsule body 51 is not communicated with the first capsule body 4, and the second capsule body 51 is adapted for accommodating the second fluid with a temperature higher than that of the first fluid during the cryoablation process. By designing the second capsule body 51 in an closed form, the second capsule body 51 accommodates the second fluid therein and is completely independent from the substance in the first capsule body 4, so that the temperatures of the first fluid and the second fluid can be controlled individually, therefore, such design can provide a structural basis to allow the temperature of the second fluid to stay as close to the human body temperature as possible, so as to provide the possibility of reducing the influence of the low-temperature fluid on the blood during the cryoablation process to a minimum.

Figure 5:
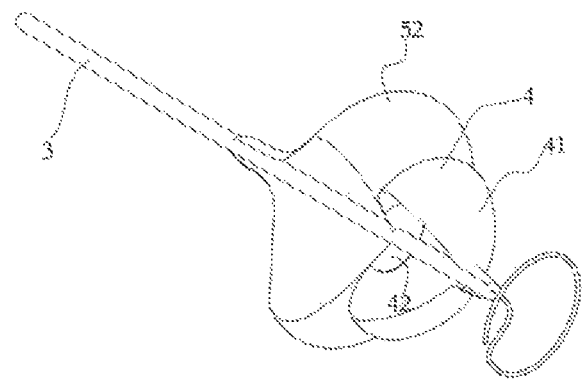
FIG. 5 is a stereogram of a fourth implementation of a cryoablation catheter provided in Embodiment 1 of the present application.

As shown in FIG. 5, as another alternative implementation of the heat insulation part 5, the heat insulation part 5 is a third capsule body 52 provided outside the rear end area 42, an outer wall of the third capsule body 52 at least partially fits to the rear end area 42, and the third capsule body 52 is adapted for accommodating the second fluid during the cryoablation process. When the third capsule body 52 is located outside the rear end area 42, because the two capsule bodies are relatively independently arranged, in one aspect, the heat conduction between the rear end area 42 and the blood can be blocked by the fitting of the third capsule body 52 onto the first capsule body 4, in another aspect, the two spaced capsule bodies are easier to manufacture, so that the use cost of the consumptive material of capsule bodies can be reduced.

As an improved implementation of the third capsule body 52, the third capsule body 52 has a maximum outer diameter larger than that of the first capsule body 4. When the maximum outer diameter of the third capsule body 52 is larger than the maximum outer diameter of the first capsule body 4, in one aspect, during the cryoablation process, the third capsule body 52 can abut against the opening of the pulmonary vein, with the first capsule body 4 slightly protruding into the pulmonary vein, such a form can have a better blocking effect, wherein the third capsule body 52 on the side of the atrium can completely block the blood from contacting the first capsule body 4; in another aspect, the third capsule body 52 also has certain positioning effect to allow the entire capsule body assembly to more smoothly fit to the opening of the pulmonary vein, thereby lowering the difficulty of cryoablation operation, and preventing the capsule body assembly from slipping off the target tissue during the cryoablation process.

As a further improved implementation of the cryoablation catheter, a second looping path 32 for the second fluid to be filled into or flow out of the heat insulation part 5 is provided in the core tube 3. The second looping path 32 can be utilized to circulate the second fluid during the cryoablation process, and when the circulated second fluid has a constant temperature, it can be ensured that the temperature inside the second capsule body 51 is always in a constant state, without too much fluctuation of temperature, so as to increase the stability and controllability of the operation process.

Figure 6:
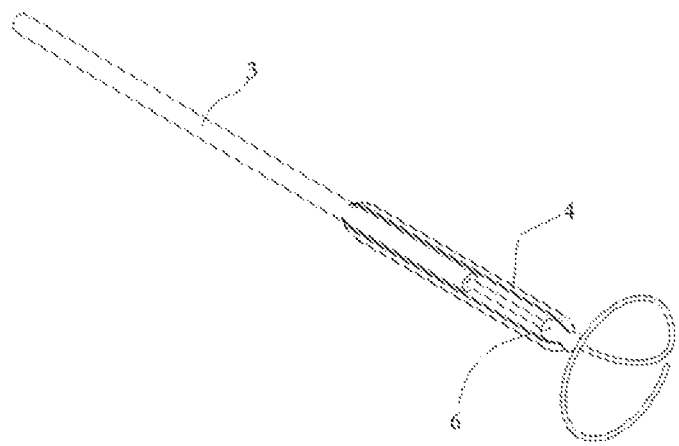
FIG. 6 is a stereogram of a cryoablation catheter provided in Embodiment 1 of the present application, with its telescopic structure in an extended state.

As shown in FIG. 6, as a further improved implementation of the cryoablation catheter, at least one telescopic structure 6 is provided at the front end of the core tube 3, the telescopic structure 6 is adapted for increasing a distance between two binding ends of the first capsule body 4 on the core tube 3 when the telescopic structure 6 protrudes out. In an initial stage at the start of the operation, the first capsule body 4 is vacuumized, and the capsule body in a thin-film state adheres to the front end of the core tube 3, at this time, the existence of the telescopic structure 6 can allow the distance between the two binding ends of the first capsule body 4 on the core tube 3 to be increased, therefore, under the action of the telescopic end thereof, the collapsed first capsule body 4 is prevented from piling up at the front end of the core tube 3 and enlarging the volume of the front end of the core tube 3, so that the cryoablation catheter can be smoothly introduced from the blood vessel into the atrium, and clogging of the blood vessel can be prevented.

As a further improved implementation of the cryoablation catheter, the core tube 3 also has a guide chamber extending in a longitudinal direction of the core tube 3 provided therein, the guide chamber can slide along a guidewire pre-positioned inside the blood vessel, and by using the guide chamber, the cryoablation catheter is able to slide along the guidewire pre-protruded into the atrium, so that it can be ensured that the cryoablation catheter is smoothly and quickly delivered into the atrium.

Embodiment 2

This embodiment provides a cryoablation operating apparatus that comprises: a handle connected to the cryoablation catheter of Embodiment 1; and an actuator connected to the core tube 3 of Embodiment 1 and adapted for driving the core tube 3 to slide in the sheath 1. During the operation process, the handle is used to manipulate the cryoablation catheter to move along a guidewire pre-protruded into the atrium, so that the cryoablation catheter moves from an incision of the body surface, along the blood vessel and into the vicinity of the target tissue. Then, the actuator is used to push the front end of the core tube 3 to protrude out of the sheath 1, and a low-temperature fluid is filled into the second capsule body 51, and after the second capsule body 51 comes into fitting contact with the target tissue, the ablation is started.

Because this embodiment comprises the cryoablation catheter of Embodiment 1, it has all the advantages corresponding to the cryoablation catheter of Embodiment 1.

Embodiment 3

This embodiment provides a cryoablation equipment. When the equipment itself has manipulation means such as a handle and an actuator, it only needs to be connected to the cryoablation catheter of Embodiment 1 to smoothly carry out the cryoablation; when the equipment itself does not have manipulation means such as a handle and an actuator, it needs to be connected to the cryoablation operating apparatus provided in Embodiment 2 to carry out the cryoablation.

Because this embodiment comprises the cryoablation catheter of Embodiment 1 or comprises the cryoablation operating apparatus of Embodiment 2, it has all the advantages corresponding to the cryoablation catheter of Embodiment 1 or the cryoablation operating apparatus of Embodiment 2.

Apparently, the aforementioned embodiments are merely examples illustrated for clearly describing the present application, rather than limiting the implementation ways thereof. For a person skilled in the art, various changes and modifications in other different forms can be made on the basis of the aforementioned description. It is unnecessary and impossible to exhaustively list all the implementation ways herein. However, any obvious changes or modifications derived from the aforementioned description are intended to be embraced within the protection scope of the present application.

The invention claimed is:

1. A cryoablation catheter, comprising:
   a first capsule body, mounted at a front end of a core tube, and having a front end area adapted for fitting to myocardial tissue during a cryoablation process and a rear end area exposed to blood;
   the core tube, having a first looping path provided therein which is adapted for a first fluid with low temperature to be filled into and flow out of the first capsule body; and
   a heat insulation part, at least partially fitting to the rear end area, adapted for reducing heat exchange efficiency between the first fluid and the blood in an atrium, wherein the heat insulation part at least covers a part of the rear end area;
   wherein the heat insulation part comprises a second capsule body provided inside the first capsule body, at least part of the second capsule body fits to an inner wall of the rear end area; and
   wherein the second capsule body has an opening at a distal end of the second capsule body communicated with an interior of the first capsule body, and the first looping path has an outflow port for the first fluid located inside the second capsule body, and wherein the core tube extends through the opening.

2. The cryoablation catheter according to claim 1, wherein the second capsule body has elasticity for supporting the first capsule body.

3. The cryoablation catheter according to claim 2, further comprising:
   a sheath, sleeved outside the core tube, and adapted for accommodating both the first capsule body and the second capsule body in a collapsed state;
   wherein the core tube is adapted for driving both the first capsule body and the second capsule body to protrude out of or retract into the sheath; and
   wherein the sheath is adapted for constraining elastic deformation of the second capsule body.

4. The cryoablation catheter according to claim 1, wherein at least one telescopic structure is provided at the front end of the core tube, the telescopic structure is adapted for increasing a distance between two binding ends of the first capsule body on the core tube when the telescopic structure protrudes out.

* * * * *